United States Patent [19]

Berger

[11] Patent Number: 4,594,354

[45] Date of Patent: * Jun. 10, 1986

[54] ANIMAL FEED COMPOSITIONS CONTAINING THE ANTIBIOTIC X-537A

[75] Inventor: Julius Berger, Passaic, N.J.

[73] Assignee: Hoffmann-La Roche Inc., Nutley, N.J.

[*] Notice: The portion of the term of this patent subsequent to Mar. 6, 1990 has been disclaimed.

[21] Appl. No.: 307,040

[22] Filed: Sep. 30, 1981

Related U.S. Application Data

[63] Continuation of Ser. No. 960,998, Nov. 15, 1978, abandoned, which is a continuation of Ser. No. 759,223, Jan. 13, 1977, abandoned, which is a continuation of Ser. No. 616,540, Sep. 27, 1975, abandoned, which is a continuation-in-part of Ser. No. 804,974, Mar. 6, 1969, Pat. No. 3,719,753, which is a continuation-in-part of Ser. No. 672,729, Oct. 4, 1967, abandoned.

[51] Int. Cl.$^4$ ............................................. A61K 31/35
[52] U.S. Cl. .................................................. 514/460
[58] Field of Search ................. 424/122, 283; 514/460

[56] References Cited

U.S. PATENT DOCUMENTS 3,150,042  9/1964  Bloss et al. ........................ 424/274
3,531,568  9/1970  Pensack ............................. 424/164
3,794,732  2/1974  Raun .................................. 424/283

FOREIGN PATENT DOCUMENTS 847887  9/1960  United Kingdom ............... 424/122

OTHER PUBLICATIONS

Berger et al.—J. Am. Chem. Soc. 73, 5295–5298 (1951).
The Merck Veterinary Manual, Second Edition, (1961), p. 843, Merck & Company.

Primary Examiner—Frederick E. Waddell
Attorney, Agent, or Firm—Jon S. Saxe; George M. Gould; William H. Epstein

[57] ABSTRACT

Compositions containing the antibiotic having the designation X-537A, useful for the treatment and prevention of coccidiosis in poultry feed compositions containing the antibiotic and methods of treating coccidiosis are disclosed.

16 Claims, No Drawings e.g., freeze-drying, spray-drying or drum drying. Furthermore, the present invention is directed to a method for avoiding the development of coccidiosis in animals, especially poultry, which involves introducing compositions containing antibiotic X-537A in its crystalline form, as its pharmaceutically acceptable salts or as its crude dried powder derived from its unfiltered broth, into the gastrointestinal tract of the animal prior to infection. Finally, this invention relates to coccidiostat compositions containing antibiotic X-537A or its pharmaceutically acceptable salts.

DETAILED DESCRIPTION OF THE INVENTION

It has been discovered that antibiotic X-537A either in its crystalline form as its pharmaceutically acceptable salts or in its amorphous form, e.g., in a freeze-dried, drum dried or spray dried powder of its unfiltered broth solids, are useful both for the prophylaxis and therapy of coccidiosis. It is especially useful by virtue of its high activity against *Eimeria tenella*, or against multiple infections, e.g., those comprising as the coccidiosis producing organisms *E. tenella, E. necatrix, E. acervulina, E. brunetti, E. maxima, E. mivati*, and the like, particularly in poultry, e.g., chickens or turkeys.

The organism producing the antibiotic useful in this invention is a Streptomyces which was isolated from a sample of soil collected at Hyde Park, Mass. and is a member of the genus of Streptomyces. Lyophilized tubes of the culture labeled with the laboratory designation X-537 have been deposited in the NRRL collection, U.S. Department of Agriculture, Agricultural Research Service, Northern Utilization Research and Development Division, Peoria, Ill. and added to its collection as NRRL 3382 where this culture has been made available to the public.

Antibiotic X-537A, the active ingredient in the compositions of this invention, can be obtained either in the form of its crystalline sodium salt when the culture is grown on a variety of media in submerged cultures or can be obtained in noncrystalline form by drying its unfiltered broth.

The antibiotic, which is isolated in the form of its sodium salt by extraction of the cells with butyl acetate, is soluble in benzene and hot petroleum ether and practically insoluble in water. According to recently obtained new data characterizing antibiotic X-537A, it has been determined that its empirical formula is $C_{34}H_{54}O_8$. The free acid in isopropyl alcohol has a characteristic ultraviolet adsorption spectrum with maxima at 317 m$\mu$ ($\epsilon$ 3700) and 249 m$\mu$ ($\epsilon$ 6400) and shows infrared spectrum main peaks (3% in $CHCl_3$) at 3410, 3030, 2960, 2860, 1705, 1650, 1460 $cm^{-1}$. It gives a positive ferric chloride reaction; it is active in vitro against gram-positive bacteria and mycobacteria but is inactive against gram-negative bacteria.

The following table summarizes the antimicrobial spectrum of antibiotic X-537A:

TABLE

| Antimicrobial Spectrum of Antibiotic X-537A | |
|---|---|
| Test Organism | Plate Units per mg. |
| Bacillus E | 800 |
| *Sarcina lutea* | 500 |
| *Staphylococcus aureus* | 20 |
| *Mycobacterium phlei* | 20 |
| Corynebacterium simplex | 20 |
| *Bacillus cereus* | 120 |
| Bacillus simplex | 20 |
| *Bacillus mesentericus* | 50 |
| *Saccharomyces cerevisiae* | 0 |
| *Scopulariopsis brevicaulis* | 0 |
| Gram-negatives* | 0 |

*These were *Pseudomonas aeruginosa, Aerobacillus polymyxa* and *Escherichia coli.*

The antibiotic is not toxic and shows no untoward side effects when used at the dosages necessary to successfully control coccidiosis. The toxic dosage of the antibiotic as tested in mice and designated as the lethal dose is as follows:

TABLE

| Mode of Administration | Lethal dose mg./kg. | Tolerated dose mg./kg. |
|---|---|---|
| Oral | 125 | 62.5 |
| Subcutaneous | 125 | 62.5 |
| Intraperitoneal | 62.5 | 50 |

The toxicity of the sodium salt of antibiotic X-537A as determined in Cornish Cross broiler type chickens and designated as $LD_{50}$ is from 59 mg./kg. body weight ±3 mg. to 84 mg./kg. ±7 mg. when administered orally as a single dose to 9 or 8 day old chicks.

The continuous feeding for nine weeks of up to 0.0125% by weight of active ingredient in the feed of the chicks has no adverse effects on their performance, based on growth, feed efficiency and mortality. At 0.025%, growth is reduced, feed conversion impaired and 25% mortality occurs.

The antibiotic can be prepared by growing the Streptomyces organisms in an aerated submerged culture. This can be done in either a shaken flask or in 50–1,000 gallon stainless steel and iron fermentation tanks. The broths are adjusted to a pH which is about neutral, i.e., 6.5–7.5 prior to being sterilized and are then incubated at slightly elevated temperatures, e.g., about 27° to 30° C., after being inoculated with spore suspensions or vegetative growth. The reaction broth is then filtered and the active material is extracted with a suitable solvent, preferably methanol, n-butanol or butyl acetate. The antibiotic activity is followed by cup-plate agar diffusion assay in which the test organism Bacillus E is employed. In general, the concentration of antibiotic required to produce an inhibition zone of 20–22 mm. in diameter with any of the test organisms is considered to be 1 unit per ml. Whole broths are diluted for assay in 1% phosphate buffer, pH 6.0.

The antibiotic can be recovered without isolating it by crystallization procedures. This is accomplished, e.g., by placing the fermentation broth, without filtering, into trays and completely freezing the broth in a deep freeze followed by placing the frozen broth in a freezer dryer and dehydrating from the frozen state. After dehydration, the crude solids are recovered in powder form. The recovered solids contain about 1% to 2% bioassay of the pure antibiotic. The fermentation broth can also be dried by drum drying or spray drying to obtain a crude powder containing about 1% to 2% bioassay of the pure antibiotic.

The growth of the Streptomyces organism can be supported on a variety of media which results in antibiotic production. Examples of suitable media are those containing complex nitrogen sources such as soyflour, fishmeal, distillers residues, and cottonseed meal. These

ANIMAL FEED COMPOSITIONS CONTAINING THE ANTIBIOTIC X-537A

RELATED APPLICATIONS

This application is a continuation application of Ser. No. 960,998 filed Nov. 15, 1978, now abandoned, which is a continuation application of Ser. No. 759,223 filed Jan. 13, 1977, now abandoned, which is a continuation application of Ser. No. 616,540, filed Sept. 25, 1975, now abandoned, which is a continuation application of Ser. No. 252,788 filed May 12, 1972, now abandoned, which is a continuation-in-part application of Ser. No. 804,974, filed Mar. 6, 1969, now U.S. Pat. No. 3,719,753, which is a continuation-in-part application of Ser. No. 672,729 filed Oct. 4, 1967, now abandoned. The benefit of the priority dates of the aforesaid applications is hereby claimed.

BACKGROUND OF THE INVENTION

Coccidiosis, especially poultry coccidiosis, is a major problem in the poultry industry and if not controlled mortality and morbidity caused thereby effect serious economic loss in the raising of poultry.

Coccidiosis is a disease caused by a protozoa parasite of microscopic size called *coccidia*, belonging to the genus Eimeria. It is specific to the host animal. Thus, the finding that a cocidiostat agent is suitable for use against one species of Eimeria in a host of a specific species does not necessarily carry with it the implication that it will be equally effective against other species of Eimeria in the same or other species of hosts. In fact, many coccidiostatic agents, while being effective against a specific species of Eimeria in a host animal, will not evidence this efficacy against other species of Eimeria in the same host animal.

Coccidiosis affects most animals raised commercially for food purposes, particularly poultry, such as turkeys, ducks, chickens and the like; sheep, cattle, swine, etc. are also affected. For example, in the poultry industry, no problems are more serious and more common than those resulting from parasitic diseases such as coccidiosis. The problem is especially great in this industry since the new techniques for raising poultry require that the birds be confined to narrow environs and, thus, be raised under crowded conditions. This close proximity of the birds while being raised is conductive to coccidiosis infections and the rapid spread thereof.

Infection is caused by the invasion of the animals by the protozoa parasite, coccidia. The infection in the host animals is initiated by the ingestion, usually along with feed or water, of Eimeria organisms in the sporulated oocyst stage. When the ingested oocysts enter the intestine, the infectious stage of the Eimeria soon develops from the oocysts and causes extensive damage to the inner walls of the intestine and the cecum or "intestinal pouch". There are both chronic and acute forms of coccidiosis infection in chickens. One type called cecal coccidiosis is caused primarily by the organism E. tenella and results in the destruction of the cecal linings of the host. Intestinal coccidiosis in chickens results primarily from other species of Eimeria and is equally as serious from an economical point of view. Such species of Eimeria are exemplified by *E. necatrix, E. acervulina, E. maxima, E. brunetti, E. hagani, E. praecox, E. mitis,* etc. Other organisms, such as *E. gallopavonis, E. meleagrimitis, E. adenoeides, E. meleagridis, E. dispersa, E. innocua, E. subrotunda,* etc. cause coccidiosis infections in turkeys. In the duck and goose, *E. truncata, E. anseris,* etc.; in cattle, *E. bovis, E. zurnii, E. alabamensis, E. auburnensis,* etc.; in sheep, *E. ahsata, E. parva, E. faurei, E. arloingi,* etc.; in pigs, *E. debliecki, E. spinosa,* etc. cause coccidiosis. Thus, it is apparent from the above that the various species of Eimeria cause infection to a type specific to host animals.

In poultry, e.g., chickens and turkeys, in an outbreak of coccidiosis, the flock becomes seriously infected with little or no forewarning and a very high mortality can result unless the birds are promptly treated. Animals that do survive these types of infections are usually of lessened economical value inasmuch as they are quite inefficient in converting feed to weight gains, grow much more slowly than normal animals and frequently appear listless.

As is noted above, coccidiosis is, additionally, a disease problem in other larger animals such as lamb, sheep, calf, cattle and pigs, although of less concern than it is in the poultry industry. However, an awareness is currently developing in connection with the raising of these animals of the effect of coccidiosis thereon from an economical point of view, and the concerned people in the field are beginning to recognize that the problems resulting from an outbreak of coccidiosis should not be overlooked. In such an outbreak in larger animals, the herd also becomes seriously infected with little or no forewarning. It is readily apparent that even a low mortality rate in a herd of larger animals from coccidiosis has serious economic consequences due to the large loss incurred per animal unit.

A number of coccidiostatic agents are presently available for either the therapy or prevention of coccidiosis and some of these agents are effective in preventing high mortality among the infected animals. Still, outbreaks of coccidiosis among the animals occur due, in some cases, to the development of resistance of the Eimeria to known occcidiostats. Furthermore, animals treated with certain known coccidiostats sometimes show a lower feed efficiency and less rapid weight gains than healthy animals. Moreover, many of the known coccidiostats have been found to possess a limited anticoccidial species spectrum and they are also often too expensive for wide use such as in poultry husbandry, particularly in view of the high concentration levels at which they must be used in order to achieve the desired end.

Therefore, a definite need exists for an antiparasitic composition which is effective in the treatment and control of coccidiosis caused by a broad spectrum of Eimeria organisms in animals but which does not suffer from the defect of lowering the feed efficiency and growth. Furthermore, greatly desired from the animal raisers point of view, is a highly effective coccidiostat which is well tolerated by the host.

SUMMARY OF THE INVENTION

The present invention, therefore, is directed to a method of treating coccidiosis in animals, advantageously poultry, especially turkeys and chickens, by introducing into the gastrointestinal tract of the animal infected with a causative pathogenic agent of the disease, a therapeutic amount of the antibiotic designated in the laboratory as X-537A in its crystalline form as its pharmaceutically acceptable salts, e.g., its alkali metal salts, i.e., sodium, potassium and the like, or as its crude dried powder obtained from unfiltered broth solids by, media will support production of antibiotic with 30–400 units of activity. Synthetic media generally are unsatisfactory since low yields result.

The pharmaceutically acceptable salts of antibiotic X-537A can be prepared by conventional means. Among such salts, are the alkali metal salts, alkaline earth metal salts, and organic salts. Of these the sodium, potassium and calcium salts are preferred. The salts are formed by conventional means, i.e., the sodium salt is prepared by reaction of the antibiotic with sodium carbonate and the potassium salt is prepared by reaction of the antibiotic with potassium carbonate.

The coccidiostat compositions of this invention containing as the active ingredient, crystalline antibiotic X-537A, or its pharmaceutically acceptable salts, or the dried unfiltered broth are prepared by mixing the active ingredient with an inert ingredient. The inert ingredient can comprise a feedstuff, extender materials and the like. By the term "inert ingredient" is meant a material which does not function as an antiparasitic agent, e.g., a coccidiostat, is inactive with respect to the active ingredient and which may be safely ingested by the animals to be treated, and thus, such inert material is one which is inactive for the purpose of the present invention.

The active ingredient when orally administered to coccidiosis susceptible domestic fowl, particularly turkeys and chickens, as a component of feed, effectively controls the disease by either preventing it or curing it after it occurs. Furthermore, the treated fowl either maintain their weight or actually gain weight when compared to controls. Thus, the compositions of this invention not only control coccidiosis, but also, aid in improving the efficiency of conversion of feed to weight gains.

The actual concentration of the active ingredient in animal feed can, of course, be adjusted to the individual needs and may vary over a wide range. The limiting criteria of the concentration are that the minimum concentration is such that a sufficient amount of active ingredient is provided to effect the desired control of coccidiosis and the maximum concentration is such that the amount of composition ingested does not result in any untoward or undesirable side effects.

Thus, for example, a feed premix or complete feed contains sufficient active ingredient to provide from about 0.001% to about 0.0125% by weight of the daily feed consumption. Preferably, about 0.00312% to 0.00625% by weight is used. Generally, about 0.005% to about 0.006% of the active ingredient is sufficient for the purpose of controlling and combating coccidiosis. Amounts greater than 0.0125%, while being effective against coccidiosis, do not generally show improved results over 0.0125% and in some cases may adversely affect the growth, feed efficiency and mortality.

Even though amounts over 0.00625% are efficacious for combating coccidiosis, this amount is the preferred upper range because of economics, i.e., the cost per unit of effectiveness is lowest within this range. Amounts lower than 0.001% and in some cases lower than 0.003% are not effective for combating coccidiosis. Preferred is a lower limit of 0.00312% because this insures efficaciousness. The most preferred amount, i.e., about 0.005% to about 0.006% by weight of the poultry daily feed consumption is particularly efficacious since it achieves maximum effect with minimum dose. The range of the weight amounts of active antibiotic in the dried unfiltered broth solids which are efficacious for combating coccidiosis is the same as for the crystalline material or its salts. For example, when administered in feed to chicks so as to contain a dosage of 0.003% of active ingredient, the crude dried unfiltered broth results in an average degree of infection of 1.4 while at the same dosage, the sodium salt of the crystalline antibiotic results in an average degree of infection of 1.7. At a dosage equivalent to a concentration of active ingredient of 0.006%, the dried material results in an average degree of infection of 0.0 while the sodium salt of the crystalline antibiotic results in an average degree of infection of 0.2.

The optimum dose level will, of course, vary with the size of the animal. When using antibiotic X-537A in accordance with the invention for treating or preventing coccidiosis, it can be first compounded or blended with a feed ingredient or carrier to become a feed additive premix, a feed concentrate, or a feed additive supplement. A feed additive, concentrate or premix is an article intended to be diluted to produce a complete feed, i.e., an article intended to be administered as a sole ration. A feed additive supplement is an article intended for consumption by an animal directly or which can be further diluted to produce a complete feed or can be ingested and used as a supplement to other rations. Feed additive supplements, concentrates and premixes contain a relatively large percentage of coccidiostats, i.e., the active ingredient, and are conveniently prepared by adding the active ingredient to a suitable carrier and mixing in a manner to give substantially uniform dispersion of the coccidiostat in the carrier. Suitable carriers are solids that are inert with respect to the active ingredient and which may safely be ingested by the animals to be treated. The nutrient carriers used as poultry feeds and, for the purpose of this invention, as carriers for the antibiotic X-537A will vary to some extent depending upon the specific needs of the type of poultry being fed and on the final use being made of the animals. However, for the most part, these feeds will contain sources of protein, such as fish meal, soybean meal, corn, peanut products and the like; and sources of carbohydrates, such as grains, meals, flours, sugars and the like. In addition, the mineral and vitamin balances for the animal can be maintained by the incorporation into the feed of the required minerals, i.e., sodium, potassium, magnesium, calcium carbonate, etc. and vitamins, e.g., vitamin A, $B_{12}$, D and thiamine. Of course, the food may also contain other conventional feed additives. Typical of such carriers are commercial poultry feeds, ground cereal grains, grain by-products, plant protein concentrates, (soy, peanuts, etc.) fermentation by-products, salt, limestone, inorganic compounds, and the like or admixtures thereof. Liquid dispersions can be prepared by using water or vegetable oil preferably including a surface active agent, emulsifying agent, and the like in the liquid dispersion such as ethylene diamine tetraacetic acid, etc. and solubilizers. Any suitable carrier or extender material can function as the inert ingredient in the solid form of the antiparasitic agent provided that it is inert to the active material and is nontoxic insofar as the animal to which it is to be administered is concerned.

The active ingredient may be blended into a mash, pellet, or any desired configuration with the inert carrier or extender solid material by any convenient technique. For example, compositions can be formed by finely grinding or pulverizing the active ingredient and the inert ingredient using any commercially available grinder or pulverizer with or without the feed material being present. If the feed material is not present when the grinding or pulverizing is effected, the resultant material can be distributed, in accordance with the present invention, in any conveniently available feed material. Typical poultry feeds which can be medicated with the active ingredient of this invention can contain several ingredients, for example, they can contain high energy grain products such as corn, wheat, wheat red dog flour, milo, oatmeal, or the like; medium and low energy grain products, such as oats, barley, wheat flour, middlings, standard middlings or the like; stabilized fats; vegetable protein such as soybean meal, corn gluten meal, peanut meal, or the like; animal protein such as fish meal, fish solubles, meat scraps or the like; UFG (unidentified growth factor) soures and other B-vitamin carriers such as dried milk products, dried brewers yeast, distillers dried solubles, fermentation solubles, or the like; dehydrated alfalfa meal; and various special additives such as additional riboflavin, vitamin $B_{12}$, calcium pantothenate, niacin, choline, vitamin K and vitamin E or the like, as well as stabilized vitamin A, vitamin $D_3$ (D-activated animal sterols); calcium and phosphorus supplements such as dicalcium phosphate, steamed bone meal, defluorinated phosphate, limestone, or the like; iodized salt, manganese sulfate, zinc carbonate, an antibiotic feed supplement; methionine or its hydroxy analog, and an antioxidant.

As is evident from the above, the coccidiostat compositions are intended for oral ingestion. They can be added to the normal feed supply of the treated animal or can be administered by other procedures, such as incorporating the same in a tablet, pill, or bolus and supplying it forcibly to the animal. The administration of the active ingredient must be considered in terms of the specific animal under the husbandry practices encountered.

The invention is further illustrated by the following examples.

EXAMPLE 1

Preparation of Crystalline Antibiotic X-537A

The Streptomyces organism was grown in aerated submerged culture in shaken flasks. The pH of the broth was adjusted by the addition of KOH solution to 6.5–7.5, then the broth was sterilized. A tank fermentation was used wherein a 5–10% inoculum consisting of 3 day old submerged growth from aerated bottles was used in the tank. The medium contained 2% soybean flour, 2% brown sugar, 0.5% $K_2HPO_4$. The fermentation was carried out at 28° C., under positive air pressure, with air-flows of 5–10 cu. ft. of air per minute per 40 to 80 gallon liquid charge. The broth was harvested after 4 to 6 days fermentation, filtered, and the antibiotic was recovered by extraction. The extraction was carried out as follows:

204 Liters of broth were filtered and the wet filter cake was suspended in 100 liters of butyl acetate and the mixture was stirred overnight, at room temperature. The mixture was then filtered and the water layer was separated and discarded. The butyl acetate solution, assaying 30 million Bacillus E units, was concentrated in vacuo to 3 liters, washed with 10% sodium carbonate solution, and dried with anhydrous sodium sulfate.

On further concentration to 300 ml. and dilution with 350 ml. of petroleum ether (b.p. 50°–60° C.), 41 g. of solid material, assaying 25 million Bacillus E units, separated. This solid material was then extracted in a Soxhlet apparatus with 4 liters petroleum ether (b.p. 50°–60° C.) for 40 hours. The extract was taken to dryness in vacuo, the crystalline residue suspended in petroleum ether and filtered, yielding 24.49 g. assaying 500 E units per mg.: total 12.25 million E units. The mother liquor of the solid yielded an additional 5.73 grams of the crystalline antibiotic.

After recrystallization from ether-petroleum ether, this material which contained sodium, was dissolved in ether and washed with dilute sulfuric acid to convert it to the free acid. Removal of the ether left an oily residue which crystallized from ethanol. Several recrystallizations from ethanol did not change the melting point which remained unsharp at 100°–109° C.; $[\alpha]_D^{26} -7.2°$ (methanol, c=1); assay 800 E units per mg. The ultraviolet adsorption spectrum of the free acid showed maxima at 317 m$\mu$ ($\epsilon$ 3700) and 249 m$\mu$ ($\epsilon$ 6400) in isopropyl alcohol. The acid was soluble in organic solvents and insoluble in water, but could be obtained in crystalline condition only from alcohols, from which it appeared to crystallize with one or more molecules of solvent. The solvent could be removed by heating to 100° C. at reduced pressure. With alcoholic ferric chloride a green-blue coloration was obtained. The anthrone test for carbohydrate was negative. It contained no nitrogen or halogen, phosphorus or sulfur, and on combustion left no ash.

The compound was analyzed with the following results according to recently obtained new data:

Analysis: Calculated for $C_{34}H_{54}O_8$: C, 69.12; H, 9.21; O, 21.67. Found: C, 68.88; H, 9.48; O, 21.73.

A sample recrystallized twice from isopropyl alcohol also melted at 100°–109° C. and was analyzed with the following results according to recently obtained new data:

Analysis: Calculated for $C_{34}H_{54}O_8$: C, 69.12; H, 9.21; for $C_{34}H_{54}O_8 \cdot C_3H_7OH$: C, 68.27; H, 9.60; for $C_{34}H_{54}O_8 \cdot 2C_3H_7OH$: C, 67.57; H, 9.93. Found (dried at 50° C.): C, 67.60; H, 9.32. Found (dried at 60° C.): C, 68.24, 68.24; H, 9.35, 9.26.

EXAMPLE 2

Sodium salt of crystalline antibiotic X-537A

The sodium salt was prepared by shaking an ether solution of the free acid with aqueous sodium carbonate. The salt which remained in the ether was recrystallized twice from benzene-ligroin and dried. It had a melting point, taken in an open capillary tube, of 191°–192° C. dec.

The salt was analyzed with the following results according to recently obtained new data:

Calculated for $C_{34}H_{53}O_8Na$: C, 66.65; H, 8.70. Found (dried at 78° C.): C, 66.65; H, 8.89.

Upon analysis, for a calculated equivalent weight of 610.7, an equivalent weight of 604 was found by electrometric titration.

The ultraviolet absorption spectrum of the sodium salt in isopropyl alcohol showed a maximum at 308 m$\mu$ ($\epsilon$ 4100) and an inflection at about 245 m$\mu$.

The infrared spectrum of the sodium salt shows the following main peaks: (3 percent in $CHCl_3$) 3500–3100 (broad), 3000, 2960, 2940, 2875, 1710, 1600, 1580, 1460, 1440, 1390, 1380 cm$^{-1}$.

EXAMPLE 3

Potassium Salt of Crystalline Antibiotic X-537A

The potassium salt was prepared by shaking an ether solution of the free acid with aqueous potassium carbonate, drying and removing the ether in vacuo. The residue was recrystallized twice from petroleum ether and dried in vacuo at 100° C. The compound has a melting point of 177°-178° C.

Upon analysis, the following results were obtained according to recently obtained new data:

Calculated for $C_{34}H_{53}O_8K$: C, 64.94; H, 8.48; K, 6.22. Found: C, 65.23, 65.55; H, 9.17, 8.94; K, 6.17, 6.24.

EXAMPLE 4

Preparation of Dried Unfiltered Broth of Antibiotic X-537A

Agar slants were prepared to contaain medium of the following composition (in grams per liter): canned tomato paste,20; defatted soy flour (soyalose 103), 10; technical glucose, 10; calcium carbonate, 2; bacteriological peptone (Wilson Medo peptone) 1; dipotassium phosphate, 1; granulated agar 20. The medium was adjusted to pH 7.0 before sterilization.

A number of slants were inoculated with spores and mycelium of the Streptomyces and incubated at 28° C. for about 7 days. By this time the slants were heavily sporulated. Loopfuls of spores were transferred to replicate 400 ml. quantities of medium contained in 2000 ml. conical flask fitted with bottom outlets. The medium contained, in grams per liter: Brown sugar, 20; defatted soybean meal (Soyalose 103) 20; corn steep liquor, 5; lard oil, 2; dipotassium phosphate, 1.0. The medium was brought to pH 7.0 before sterilization. After inoculation, the flasks were incubated at 28° C. on a rotary shaker which provided agitation at 240 RPM in a one inch horizontal circular orbit.

After 5 days of incubation 200 ml. quantities of the heavy growth which had developed were transferred aseptically to 8.5 liter quantities of medium contained in 14 liter New Brunswick stirred jar fermentors. The fermentor medium contained, in grams per liter: cottonseed meal, 5; corn starch, 5; corn steep liquor, 5; soybean oil, 10; disodium phosphate, 1. The medium was adjusted to pH 7.0 before sterilization and then autoclaved at 120° C. for 45 minutes.

After inoculation four replicate stirred jar fermentors were incubated at 28° C. while aerating at the rate of 4 liters per minute and agitating at a shaft speed of 500 RPM. Sterile soybean oil was added as needed to control frothing.

After incubating for 212 hours, the broth potencies had reached maximum values and the fermentors were harvested. The broths were combined and mixed thoroughly to achieve homogeneity.

Two to 2.5 liter quantities of the unfiltered broth were placed into flat bottom stainless steel trays and frozen in a deep freeze. When the broth was completely frozen, the trays were placed in a freeze dryer and dehydrated from the frozen state.

After dehydration the solids recovered were pooled and homogenized. The recovered freeze dried solids were assayed and found to contain about 10.8 mg. of antibiotic X-537A per gram.

EXAMPLE 5

This example illustrates the utilization of the antibiotic coccidiostat in an animal feed. A medicated poultry feed intended as a starter feed for broilers is prepared by blending 0.005% by weight of antibiotic X-537A in a basic poultry ration consisting of:

| Ingredients | Pounds per Ton |
|---|---|
| Corn meal, No. 2, yellow, ground | 1123 |
| Stabilized grease or vegetable oil | 60 |
| Soybean oil meal (low fiber content 50% protein) | 480 |
| Corn Gluten meal | 50 |
| Fish meal, antioxidant treated, 60% protein | 30 |
| Fish solubles, dried basis | 10 |
| Meat and bone scraps, 50% protein | 140 |
| Corn distillers dried solubles | 50 |
| Alfalfa meal, 17% protein 100,000 A./lb. | 30 |
| Salt, iodized | 5 |
| Manganese sulfate, feed grade | 0.75 |
| Zinc carbonate or oxide | 0.25 |
| Riboflavin, Grams | 3 |
| Vitamin $B_{12}$, mg. | 6 |
| Calcium pantothenate, gms. | 5 |
| Niacin, gm. | 30 |
| Stabilized vitamin A USP units | 6,000,000 |
| Vitamin $D_3$, IC units | 650,000 |
| Vitamin E acetate, IU | 5,000 |
| Vitamin E, (menadione sodium bisulfite) gms. | 2 |
| DL-methionine or hydroxy analog, pound | 1 |
| Antioxidant (ethoxyquin or butylated hydroxy toluene) lb. | 0.25 |

Similar feeds can be prepared containing the antibiotic at other concentrations, for example, containing from 0.001 percent to 0.0125 percent by weight of said compound as well as in the form of the dried unfiltered broth in such amount as to give the same concentrations of active antibiotic.

The following tests were carried out to determine the activity of antibiotic X-537A.

A. *Eimeria tenella* infection in laboratory chickens Test Method

This test utilizes ten chickens per drug group. Ten chickens are employed as a weight control and ten chickens as an infected control. The drug is given 48 hours in advance of the infection. One gm. of the test drug is mixed in a mechanical mixer with a sufficient amount of chicken feed to result in the desired dosage. The infection consists of approximately 200,000 oocysts given orally by pipette. The tests lasts for eleven days and then the surviving birds are autopsied and examined for gross lesions in the ceca. The test birds are rated according to the number of survivors and the number of cecal lesions. The results are expressed as average degree of infection (A.D.I.). An average degree of infection of less than 2.5 is considered significant.

| Compound | Dosage in Feed % | Average Degree of Infection | | % Mortality | | Weight Gain % | |
|---|---|---|---|---|---|---|---|
| | | Treated | Untreated | Treated | Untreated | Treated | Untreated |

Results of Test I

-continued

| Compound | Dosage in Feed % | Average Degree of Infection | | % Mortality | | Weight Gain % | |
| --- | --- | --- | --- | --- | --- | --- | --- |
| | | Treated | Untreated | Treated | Untreated | Treated | Untreated |
| Uninfected untreated control | None | | 0.0 | | 0 | | 100 |
| Infected untreated control | None | | 3.0 | | 25 | | 68 |
| Crystalline antibiotic | 0.00625 | 0.4 | | 0 | | 92 | |
| X-537 A | 0.00312 | 2.2 | | 0 | | 85 | |
| Results of Test II | | | | | | | |
| Uninfected untreated control | None | | 0.0 | | 0 | | 100 |
| Infected untreated control | None | | 2.9 | | 30 | | 83 |
| Crystalline antibiotic | 0.006 | 0.1 | | 0 | | 95 | |
| X-537 A | 0.005 | 0.8 | | 5 | | 94 | |
| | 0.004 | 1.7 | | 15 | | 87 | |
| | 0.003 | 2.2 | | 5 | | 85 | |
| | 0.002 | 2.6 | | 15 | | 83 | |
| | 0.001 | 2.8 | | 15 | | 80 | |
| Results of Test III | | | | | | | |
| Uninfected untreated control | None | | 0 | | 0 | | 100 |
| Infected untreated control | None | | 3.2 | | 30 | | 48 |
| Crystalline antibiotic | 0.006 | 0.2 | | | | 97 | |
| X-537 A | 0.005 | 0.5 | | | | 98 | |
| | 0.004 | 1.1 | | | | 81 | |
| | 0.003 | 1.7 | | | | 79 | |
| Concentration of active ingredient in Dried Unfiltered Broth with 1.08 percent by weight Bioassay of antibiotic X-537 A | 0.006 | 0 | | 0 | | 91 | |
| | 0.005 | 0 | | 0 | | 90 | |
| | 0.004 | 0.4 | | 0 | | 92 | |
| | 0.003 | 1.4 | | 10 | | 89 | |

As can be seen from the data in the table the antibiotic is effective at the preferred dosages illustrated for the treatment of coccidiosis. It should also be noted from the data in the table that the use of antibiotic as a coccidiostat does not substantially adversely affect the conversion of feed to weight gain.

B. Multiple Eimeria infections in chickens Test Method

The test method is the same as for *Eimeria tenella*. The multiple Eimeria infections tested herein are mixtures of *E. tenella, E. necatrix, E. acervulina, E. brunetti, E. maxima, E. mivati* infections.

| Results of Test Compound | Dosage in Feed % | Average Degree of Infection | | % Mortality | | Weight Gain % | |
| --- | --- | --- | --- | --- | --- | --- | --- |
| | | Treated | Untreated | Treated | Untreated | Treated | Untreated |
| Uninfected untreated control | None | | 0.0 | | 0 | | 100 |
| Infected untreated control | None | | 3 | | 50 | | 62 |
| Crystalline antibiotic | 0.00625 | 0.0 | | 0 | | 108 | |
| X-537 A | 0.00312 | 0.9 | | 0 | | 105 | |

As can be seen by the results in the foregoing table the antibiotic is effective in treating multiple coccidiosis infections and is further significant in causing greater than expected efficiency of conversion of feed to weight gain in the chickens, thus indicating that there is some synergistic effect present.

I claim:

1. A coccidiostatic poultry feed additive premix comprising a poultry feed material and, as the active ingredient, sufficient amount of antibiotic X-537A or a pharmaceutically acceptable salt thereof to provide, upon addition of the premix to a conventional poultry feed, a poultry feed containing, per 100 parts by weight of feed, from about 0.001 parts to about 0.0125 parts of the active ingredient.

2. The poultry feed additive premix of claim 1 which contains sufficient amount of the active ingredient to provide, upon addition of the premix to a poultry feed, from about 0.00312 parts to about 0.00625 parts of the active ingredient per 100 parts by weight of feed.

3. The poultry feed additive premix of claim 1 which contains sufficient amount of the active ingredient to provide, upon addition of the premix to a poultry feed, from about 0.005 to about 0.006 parts of the active ingredient per 100 parts by weight of feed.

4. The poultry feed additive premix of claim 1 wherein the active ingredient is crystalline antibiotic X-537A.

5. The poultry feed additive premix of claim 1 wherein the active ingredient is a dried powder containing antibiotic X-537A in non-crystalline form, said dried powder obtained from drying the product of an antibiotic X-537A fermentation.

6. A coccidiostatic poultry feed which is useful for treating or preventing coccidiosis, having dispersed therein, as an active ingredient, from about 0.001 parts to about 0.0125 parts of antibiotic X-537A or pharmaceutically acceptable salts thereof per 100 parts by weight of the feed.

7. The poultry feed of claim 6 wherein the amount of active ingredient present is from about 0.00312 parts to about 0.00625 parts.

8. The poultry feed of claim 6 wherein the amount of active ingredient present is from about 0.005 to 0.006 parts.

9. The poultry feed of claim 6 wherein the active ingredient is crystalline antibiotic X-537A.

10. The poultry feed of claim 6 wherein the active ingredient is a dried powder containing antibiotic X-537A in non-crystalline form, said dried powder obtained from drying the product of an antibiotic X-537A fermentation.

11. A feed additive premix, for animals raised commercially for food, comprising an animal feed material and, as the active ingredient, sufficient amount of antibiotic X-537A or a pharmaceutically acceptable salt thereof to provide, upon addition of the premix to a conventional animal feed, an amimal feed containing, per 100 parts by weight of feed, from about 0.001 parts to about 0.0125 parts of the active ingredient.

12. An animal feed additive premix of claim 11 wherein the active ingredient is crystalline antibiotic X-537A.

13. The animal feed additive premix of claim 11 wherein the active ingredient is a dried powder containing antibiotic X-537A in noncrystalline form, said dried powder obtained from drying the product of an antibiotic X-537A fermentation.

14. An animal feed composition, for animals raised commercially for food, which comprises an animal feed and as an active ingredient an antibiotic X-537A or pharmaceutically acceptable salts thereof, said antibiotic being present in an amount of from about 0.001 parts to about 0.0125 parts per 100 parts of an animal feed composition.

15. The animal feed composition of claim 14 wherein antibiotic X-537A is present in crystalline form.

16. The animal feed composition of claim 14 wherein antibiotic X-537A is present in noncrystalline form in a dried powder, said dried powder obtained from drying the product of an antibiotic X-537A fermentation.

* * * * *

UNITED STATES PATENT AND TRADEMARK OFFICE
CERTIFICATE OF CORRECTION

PATENT NO. : 4,594,354

DATED : Jun. 10, 1986

INVENTOR(S) : Berger

It is certified that error appears in the above—identified patent and that said Letters Patent is hereby corrected as shown below:

Title page:

Related U.S. Application Data

[63] Continuation of Ser. No. 960,998, Nov. 15, 1978, abandoned, which is a continuation of Ser. No. 759,223, Jan. 13, 1977, abandoned, which is a continuation of Ser. No. 616,540, Sep. 27, 1975, abandoned, which is a continuation of Ser. No. 252,788, May 12, 1972, abandoned, which is a continuation-in-part of Ser. No. 804,974, Mar. 6, 1969, Pat. No. 3,719,753, which is a continuation-in-part of Ser. No. 672,729, Oct. 4, 1967, abandoned.

Signed and Sealed this

Seventh Day of October, 1986

[SEAL]

Attest:

DONALD J. QUIGG

Attesting Officer

Commissioner of Patents and Trademarks